(12) United States Patent
Buehler

(10) Patent No.: US 11,452,825 B2
(45) Date of Patent: Sep. 27, 2022

(54) INHALER ARTICLE WITH OCCLUDED AIRFLOW ELEMENT

(71) Applicant: PHILIP MORRIS PRODUCTS S.A., Neuchâtel (CH)

(72) Inventor: Frederic Ulysse Buehler, Neuchâtel (CH)

(73) Assignee: Philip Morris Products S.A., Neuchatel (CH)

(*) Notice: Subject to any disclaimer, the term of this patent is extended or adjusted under 35 U.S.C. 154(b) by 418 days.

(21) Appl. No.: 16/612,543

(22) PCT Filed: May 22, 2018

(86) PCT No.: PCT/IB2018/053619
§ 371 (c)(1),
(2) Date: Nov. 11, 2019

(87) PCT Pub. No.: WO2018/220475
PCT Pub. Date: Dec. 6, 2018

(65) Prior Publication Data
US 2020/0197637 A1    Jun. 25, 2020

(30) Foreign Application Priority Data
May 31, 2017    (EP) .................................... 17173762

(51) Int. Cl.
*A61M 15/00*    (2006.01)
*A61M 15/06*    (2006.01)
(Continued)

(52) U.S. Cl.
CPC ......... *A61M 15/0028* (2013.01); *A24F 40/05* (2020.01); *A24F 40/485* (2020.01);
(Continued)

(58) Field of Classification Search
CPC .......... A61M 15/0028; A61M 15/0021; A61M 15/0036; A61M 15/06; A61M 2202/064;
(Continued)

(56) References Cited

U.S. PATENT DOCUMENTS 3,888,253 A    6/1975    Watt et al.
4,338,931 A *  7/1982    Cavazza ........... A61M 15/0036
                                                128/203.15
(Continued)

FOREIGN PATENT DOCUMENTS

CN    1317995    10/2001
CN    101489612    7/2009
(Continued)

OTHER PUBLICATIONS

Russian Office Action and Search Report for RU 2019143705 issued by the Patent Office of the Russian Federation dated Jul. 9, 2021; 13 pages including English Translation.
(Continued)

*Primary Examiner* — Elliot S Ruddie
(74) *Attorney, Agent, or Firm* — Mueting Raasch Group

(57) ABSTRACT

An inhaler article includes a tubular housing defining a holder body extending along a longitudinal axis from a mouthpiece end to a consumable receiving end. The holder body includes an inner tube extending along the longitudinal axis and within the tubular housing from a tube intake end to a tube exhaust end. The tube intake end is proximate the consumable receiving end. The inner tube defines an air flow lumen with two or more air flow apertures extending through a wall of the inner tube. An air blocking feature is positioned in the air flow lumen and between two of the air flow apertures. A vibration inducing element disposed on the inner tube proximate to the tube exhaust end or the tube intake end, the vibration inducing element comprises an
(Continued)

aperture through the wall of the inner tube and having a tapered or angled downstream aperture edge.

20 Claims, 3 Drawing Sheets

(51) Int. Cl.

| | |
|---|---|
| *A24F 40/05* | (2020.01) |
| *A24F 40/485* | (2020.01) |
| *A61K 9/00* | (2006.01) |
| *A61K 9/16* | (2006.01) |
| *A61K 31/465* | (2006.01) |
| *A24F 40/30* | (2020.01) |
| *A24F 42/20* | (2020.01) |

(52) U.S. Cl.
CPC .... *A61M 15/0021* (2014.02); *A61M 15/0036* (2014.02); *A61M 15/06* (2013.01); *A24F 40/30* (2020.01); *A24F 42/20* (2020.01); *A61K 9/0075* (2013.01); *A61K 9/1688* (2013.01); *A61K 31/465* (2013.01); *A61M 2202/064* (2013.01)

(58) Field of Classification Search
CPC . A61M 15/0005; A61M 15/003; A24F 40/05; A24F 40/485; A24F 40/30; A24F 42/20; A24F 40/40; A24F 40/20; A61K 9/0075; A61K 9/1688; A61K 31/465; A24B 15/16
See application file for complete search history.

(56) References Cited

U.S. PATENT DOCUMENTS

| | | | |
|---|---|---|---|
| 5,655,523 A | 8/1997 | Hodson et al. | |
| 6,230,707 B1 | 5/2001 | Hoerlin | |
| 7,464,706 B2 | 12/2008 | Steiner et al. | |
| 9,241,828 B2 | 1/2016 | Pardes et al. | |
| 9,380,810 B2 | 7/2016 | Rose et al. | |
| 2011/0220106 A1* | 9/2011 | Ganem | A61M 15/0028 128/203.21 |
| 2013/0340754 A1 | 12/2013 | Donovan | |
| 2014/0166004 A1 | 6/2014 | Pierro et al. | |
| 2015/0122276 A1 | 5/2015 | Johnson et al. | |
| 2016/0095355 A1 | 4/2016 | Hearn | |
| 2016/0324845 A1 | 11/2016 | Myers et al. | |

FOREIGN PATENT DOCUMENTS

| | | | |
|---|---|---|---|
| CN | 101489612 A | 7/2009 | |
| CN | 101554504 | 10/2009 | |
| CN | 103038141 | 4/2013 | |
| DE | 19502725 A1 | 8/1996 | |
| EP | 2 022 526 A1 | 2/2009 | |
| JP | H09262295 A | 10/1997 | |
| JP | 2001-187143 A | 7/2001 | |
| JP | 2015513427 A | 5/2015 | |
| JP | 2015521526 A | 7/2015 | |
| RU | 2600303 | 10/2016 | |
| WO | WO 1997/012639 A1 | 4/1997 | |
| WO | 0001494 | 1/2000 | |
| WO | 2007/121097 | 10/2007 | |
| WO | WO 2013/132056 A1 | 9/2013 | |
| WO | WO 2015/193498 A1 | 12/2015 | |
| WO | WO-2018058201 A * | 4/2018 | .......... A61M 11/001 |

OTHER PUBLICATIONS

International Search Report and Written Opinion issued by the European Patent Office for PCT/IB2018/053619; dated Aug. 7, 2018; 18 pgs.
Extended European Search Report issued by the European Patent Office for EP application No. 17173 762.0; dated Aug. 30, 2017; 8 pgs.
Cohen et al., "GRAS Flavoring Substances," 27. *GRAS Flavoring Substances. Food Technology for Flavoring Extract Manufacturers Association*, Aug. 2015:69(8):40-59.
Hall, R.L. & Oser, B.L., "Recent Progress in the Consideration of Flavoring Ingredients under the Food Additive Amendments 3. GRAS substances," *Food Technology*, Feb. 1965: p. 151-197.
International Preliminary Report on Patentability issued by the International Bureau of WIPO for PCT/IB2018/053619; dated Dec. 12, 2019; 9 pgs.
Chinese Office Action issued by the Chinese Patent Office for CN Application No. 2021880030194.6; 17 pgs. including English Translation.
Japanese Office Action for JP Application No. 2019-565528, issued by the Japanese Patent Office dated Jun. 23, 2022; 7 pgs. including English translation.

* cited by examiner

INHALER ARTICLE WITH OCCLUDED AIRFLOW ELEMENT

This application is the § 371 U.S. National Stage of International Application No. PCT/IB2018/053619, filed 22 May 2018, which claims the benefit of European Application No. 17173762.0, filed 31 May 2017, the disclosures of which are incorporated by reference herein in their entireties.

This disclosure relates to an inhaler article that includes an occluded airflow element for delivering particles, such as particles comprising nicotine, to a user.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose in a single breath.

It would be desirable to provide an inhaler article that provides particles comprising nicotine to the lungs at inhalation or air flow rates that are within conventional smoking regime inhalation or air flow rates. It would be desirable to provide deliver the particles comprising nicotine with an inhaler article that has a form similar to a conventional cigarette. It would be desirable to provide an inhaler article that is simple to manufacture and convenient to use by a consumer. It would be desirable to provide an inhaler article that is re-usable and utilizes a replaceable nicotine powder consumable article.

In one aspect, the disclosure is directed to an inhaler article comprising a tubular housing defining a holder body extending along a longitudinal axis from a mouthpiece end to a consumable receiving end. The holder body includes an inner tube extending along the longitudinal axis and within the tubular housing from a tube intake end to a tube exhaust end. The tube intake end is proximate the consumable receiving end. The inner tube defines an air flow lumen with two or more air flow apertures extending through a wall of the inner tube. An air blocking feature is positioned in the air flow lumen and between two of the air flow apertures.

The inhaler article inner tube may include a vibration element. The vibration element may include an aperture through the wall of the inner tube with a tapered or angled downstream aperture edge.

A capsule may be may be disposed onto the inner tube where the inner tube extends through opposing sides of the capsule. Preferably the air blocking feature and air flow apertures are positioned within the capsule and the tube intake end extends distally from the capsule and the tube air outlet extends proximally from the capsule.

In another aspect, the disclosure is directed an inhaler system comprising the inhaler article described herein and a nicotine powder consumable article configured to be received in the consumable receiving end of the holder body. The nicotine powder consumable article may comprise an elongated consumable body extending between a proximal end and a distal end and a capsule fixed within the elongated consumable body. The capsule preferably contains particles comprising nicotine or a pharmaceutically acceptable salt thereof. The capsule may be disposed on the inner tube. The inner tube may extend through opposing sides of the capsule, the tube intake end may extend distally from the capsule when the nicotine powder consumable article is received in the consumable receiving end of the holder body.

The nicotine powder consumable article may include a first plug of porous material disposed within the proximal end of the elongated consumable body and a second plug of porous material disposed within the distal end of the elongated consumable body. The first plug of porous material and the second plug of porous material may fix the capsule within the elongated consumable body. The second plug of porous material may contain a flavour delivery element. Preferably, the tube intake end extends into the second plug of porous material.

Providing an air blocking feature between air flow apertures may advantageously form an air flow path through a capsule. The capsule may be disposed on the inner tube and surround the air flow apertures and air blocking feature. Selective positioning of these air flow apertures along the inner tube wall may provide increased turbulence within the capsule and aid in completely emptying the capsule.

Providing a vibration inducing element on the wall of the inner tube may advantageously enable the inhalation air flow to cause or initiate a vibration along the length of the inner tube. This vibration may increase turbulence within the capsule and may reduce or prevent particle agglomeration or break up agglomerated particles, and may aid in completely emptying the capsule during consumption of the particles within the capsule.

Advantageously, providing the unique inner tube element in the described simple elongated inhaler device, along with the nicotine powder consumable article, provides an inhaler system that has a form similar to a conventional cigarette and an airflow configuration that is similar to a conventional cigarette. The inhaler system advantageously provides a reusable inhaler article with a modular and replaceable nicotine powder consumable article.

The inhaler article described herein may provide a dry powder or particles comprising nicotine to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the nicotine powder consumable article. This inhaler article may have a form similar to a conventional cigarette and may mimic the ritual of conventional smoking. This inhaler may be simple to manufacture and convenient to use by a consumer.

As used herein, the terms "upstream" and "downstream" are used to describe the relative positions of components, or portions of components, of inhalation articles and powder consumable articles described herein with respect to the direction of airflow through the inhalation articles and powder consumable articles when a user draws on the inhaler article. In particular, when a user draws on the inhaler article, air flows in the downstream direction from the tube air inlet to the mouthpiece end.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg 151-197, and in the GRAS flavoring substances 27 S. M. Cohen et al., Food Technology Aug. 2015 pg. 40-59, and intervening GRAS Flavoring Substances publications 4 to 26. For the purpose of this disclosure, nicotine is not considered as a flavourant or flavour.

The inhaler article described herein may be combined with a nicotine powder consumable article to form an inhaler system. The inhaler system may include two or more nicotine powder consumable articles. Once a first nicotine powder consumable article is consumed, a user may replace the depleted nicotine powder consumable article with a second or new nicotine powder consumable article and continue consumption of particles comprising nicotine contained within the nicotine powder consumable article. The inhaler article may be repeated utilized for 2, 10, 25, or 100 or more modular nicotine powder consumable articles.

An inhaler article includes a tubular housing defining a holder body extending along a longitudinal axis from a mouthpiece end to a consumable receiving end. The holder body comprises an inner tube extending along the longitudinal axis and within the tubular housing from a tube intake end to a tube exhaust end. The tube intake end is proximate the consumable receiving end. The inner tube defines an air flow lumen with two or more air flow apertures extending through a wall of the inner tube. An air blocking feature is positioned in the air flow lumen and between two of the air flow apertures.

The inhaler or holder body may resemble a smoking article or cigarette in size and shape. The inhaler or holder body may have an elongated cylindrical body extending along the longitudinal axis of the inhaler article. The inhaler body may have a substantially uniform outer diameter along the length of the elongated cylindrical body. The inhaler body may have a circular cross-section that may be uniform along the length of the elongated cylindrical body. The inhaler body may have an outer diameter in a range from about 5 mm to about 15 mm, or from about 7 mm to about 12 mm, or about 7 mm to about 10 mm, or about 8 mm to about 9 mm. The inhaler body may have a length (along the longitudinal axis) in a range from about 40 mm to about 100 mm, or from about 50 mm to about 90 mm, or about 60 mm to about 80 mm.

The inner tube may be configured to pierce the capsule containing particles comprising nicotine. The inner tube may have a sharp end tube distal end that facilitates piercing the capsule. Preferably the inner tube pierces opposing sides of the capsule and length of the inner tube remains extends through the entire longitudinal length of the capsule. The tube distal end may extend distally from the capsule. Preferably, the tubular housing and the inner tube are co-axial along the same longitudinal axis.

The inner tube may be configured to induce swirling or a turbulent air flow pattern within the capsule. The single inner tube may be configured to provide both an inlet air to provide inhalation air to enter the capsule and an air outlet to allow particle laden air to exit the capsule and flow to the mouthpiece portion of the inhaler article. The inner tube may not extend distally from the consumable receiving end. The inner tube may be formed of any rigid material. The inner tube may be formed of a polymeric material such a polyolefin, polyester, polyurethane. The inner tube may be formed of a metal or metallic material.

The air blocking feature may occlude the lumen of the inner tube and physically separate or isolate inlet air from outlet air within the inner tube lumen. The air blocking feature may prevent air from flowing through the air blocking feature. The air blocking feature may be an element disposed within the air flow lumen downstream from the air intake end or the air blocking feature may be a pinched feature where the inner tube is pinched such that air cannot flow through the air blocking feature. The outer diameter of the inner tube may be reduced at the pinched feature relative to the remainder of the inner tube length.

The air blocking feature may be formed of material that is different from the material forming the inner tube. The air blocking feature may be formed of the same material as the material forming the inner tube. The air blocking feature may be integrally formed with the inner tube. The air blocking feature may be formed of any air impermeable material. The air blocking feature may be formed of a rubber or polymeric material, such as polypropylene, silicone, PEEK, liquid crystal, or polyurethane, for example.

At least one air flow aperture defines a tube air outlet and is between the air blocking feature and the tube intake end. At least one air flow aperture defines an air inlet and is between the air blocking feature and the tube exhaust end. The tube exhaust end is in air flow communication with the mouthpiece end.

Air flow may enter the inhaler article via a single air inlet at the air intake end of the inner tube. Air flow may exit the inner tube ultimately from a single air outlet at the tube exhaust end. Particle laden air from the tube exhaust end is discharged into the mouthpiece end and to the consumer. Air flow may not pass thorough the inhaler tubular housing or holder body. Preferably, there are no air inlets through the inhaler tubular housing or holder body.

The location and number of air flow apertures though the wall of the inner tube may be tailored or configured to provide more or less air flow to specific locations within the capsule, as desired. Air flow apertures may be circumferentially located about the diameter of the inner tube. The airflow apertures may be uniformly placed about the circumference of the inner tube. The airflow apertures may be randomly placed about the circumference of the inner tube.

The inner tube may include at least 1, preferably at least 3 air flow apertures located upstream from and adjacent to the air blocking feature, and at least 1, preferably at least 3 air flow apertures located downstream from and adjacent to the air blocking feature. The inner tube may include at least 6 air flow apertures located upstream from and adjacent to the air blocking feature and at least 6 air flow apertures located downstream from and adjacent to the air blocking feature. The inner tube may include at least 9 air flow apertures located upstream from and adjacent to the air blocking feature and at least 9 air flow apertures located downstream from and adjacent to the air blocking feature. The inner tube may include at least 12 air flow apertures located upstream from and adjacent to the air blocking feature and at least 12 air flow apertures located downstream from and adjacent to the air blocking feature. The upstream and downstream airflow apertures may be uniformly spaced about the circumference of the inner tube. The upstream and downstream airflow apertures may be uniformly spaced along a length of the inner tube.

A majority or substantially all of the airflow thought the inhaler article flows through the inner tube. The inhaler article may be configured to enable all of or substantially all of the airflow to pass through the inner tube to the mouthpiece end. The inhaler article may be configured to isolate the mouthpiece end from the consumable receiving end except via the inner tube.

An air sealing element may be disposed within the tubular housing. The air sealing element may occlude and isolate the mouthpiece end from the consumable receiving end. The inner tube extends through the air sealing element and allows the particle laden air to pass from the capsule and inner tube contained within the consumable receiving end to the mouthpiece end. The inner tube may extend through and proximally from the air sealing element a distance.

The air sealing element may be formed of any air impermeable material. The air sealing element may be formed of a rubber or polymeric material, such as polypropylene, silicone, PEEK, liquid crystal, or polyurethane, for example. The air sealing element may be formed of same material forming the inner tube or tubular housing of the inhaler article. The air sealing element may be integrally formed with the inner tube. The air sealing element may be integrally formed with the tubular housing of the inhaler article.

A vibration inducing element may be disposed along the length of the inner tube. The vibration inducing element is activated by air flow through the inner tube. Airflow though the inner tube provides the energy that the vibration inducing element converts into vibration motion. The vibration inducing element initiates vibration of the inner tube. The vibration inducing element may induce any frequency of vibration of the inner tube. The vibration inducing element may induce a vibration frequency of the inner tube in a range from about 500 Hz to about 10000 Hz, or from about 1000 Hz to about 10000 Hz. The vibration inducing element may aid in fluidizing the particles within the capsule during inhalation. Preferably the vibration frequency is capable of breaking up agglomerated particles (within the capsule) or reduces agglomeration during aerosolization of the particles within the capsule during consumption.

The vibration inducing element may be located on the inner tube such that it is surrounded by the capsule during consumption. The vibration inducing element may be located on the inner tube such that it is outside of the capsule during consumption. The vibration inducing element may be located on the inner tube proximate to the tube exhaust end portion extending proximally from the air sealing element. The vibration inducing element may be located on the inner tube proximate to the tube intake end. Two or more vibration inducing element may be located on the inner tube.

The vibration inducing element may comprise an aperture through the wall of the inner tube and having a tapered or angled downstream aperture edge. This tapered aperture structure may induce a "reed effect" similar to a reed of a musical instrument for creating vibration. Vibration of the inner tube (and potentially of the capsule) may create turbulence and mechanical shaking of the particles within the capsule to allow complete depletion of the particles from the capsule.

The characteristics of the vibrations created by the tapered aperture structure or "reed" may be dependent of the material and the angle of the "reed" and the size of the aperture. The angle of the "reed" can vary from about 70 to about 110 degrees from the longitudinal axis, or about 85 to about 95 degrees from the longitudinal axis about 60 to about 120 degrees from the longitudinal axis. The size of the aperture may have a lateral distance in a range from about 0.05 mm to about 3 mm, or about 0.1 mm to about 1 mm or about 0.5 mm.

A capsule may be disposed on the inner tube. The capsule may define a cylindrical volume (that may have an obround shape) configured to contain particles comprising nicotine. The capsule may be formed of a metallic or polymeric material that serves to keep contaminates out of the capsule but may be pierced or punctured by the inner tube prior to consumption of the particles comprising nicotine within the capsule. The capsule may be formed of a polymer material. The polymer material may be hydroxypropylmethylcellulose (HPMC). The capsule may be a size 000 to size 4 capsule, or a size 0 to a size 2 capsule, or a size 0 capsule, or a size 1 capsule, or a size 2 capsule.

The inner tube may extend through opposing sides of the capsule. The capsule may contain particles comprising nicotine or a pharmaceutically acceptable salt thereof. Preferably, the air blocking feature and air flow apertures (extending through the wall of the inner tube) are positioned within the capsule and the tube intake end extends distally from the capsule and the tube air outlet extends proximally from the capsule. Air flow into the capsule is provided only by the air flow apertures on the inner tube located upstream from the air blocking feature occluding the inner tube. Air flow from the capsule is provided only by the air flow apertures on the inner tube located downstream from the air blocking feature occluding the inner tube. The capsule may seal around the inner tube at both locations where the inner tube is extending through the capsule.

The capsule contains nicotine particles comprising nicotine (also referred to as "nicotine powder" or "nicotine particles") and optionally particles comprising flavour (also referred to as "flavour particles"). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder.

The dry powder or powder system may have at least about 40%, or at least about 60%, or at least about 80%, by weight of the powder system comprised in nicotine particles having a particle size of about 10 micrometres or less, or 5 micrometers or less, or in a range from about 1 micrometer to about 3 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles.

Similarly, adhesion forces to particles comprising flavour may also be reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include flavour particles. The flavour particles may have any useful size distribution for inhalation delivery selectively into the mouth or buccal cavity of a user.

The powder system may have at least about 40%, or at least about 60%, or at least about 80%, by weight of the flavour of the powder system comprised in particles having a particle size of about 20 micrometres or greater. The powder system may have at least about 40% or at least about 60%, or at least about 80%, by weight of the flavour of the powder system comprised in particles having a particle size of about 50 micrometres or greater. The powder system may have at least about 40% or at least about 60%, or at least about 80%, by weight of the flavour of the powder system comprised in particles having a particle size in a range from about 50 micrometer to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. The flavour or flavourant has flavour properties that may enhance the experience of the nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

The powder system may contain carrier particles that serve to increase the fluidization of the active particles (particles comprising nicotine) since the active particles may be too small to be influenced by simple airflow though the inhaler. These carrier particles may be a saccharide such as lactose or mannitol or trehalose that may have a particle size greater than about 50 micrometres. The carrier particles may be utilized to improve dose uniformity by acting as a diluent or bulking agent in a formulation. Alternatively, the powder system utilized with the nicotine powder delivery system described herein may be carrier-free or substantially free of a saccharide such as lactose or mannitol.

The nicotine particles and a flavour may be combined or contained within the capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles or flavourant is contained outside the capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, utilizing the modular replaceable nicotine powder consumable article with the re-usable inhaler article provides a convenient and user friendly nicotine powder delivery system. The unique inner tube configuration may ensure complete depletion of the nicotine powder within the capsule or modular replaceable nicotine powder consumable article. Thus, the inhaler article may not require the elevated inhalation rates typically utilized by conventional inhalers to deliver the nicotine particles described above deep into the lungs. The modular nicotine powder consumable article may enable clean and convenient disposal of the depleted modular nicotine powder consumable article.

An inhaler system may include the inhaler article, as described herein, and a nicotine powder consumable article configured to be received in the consumable receiving end of the holder body. The nicotine powder consumable article may be described as a "modular" element that may be easily mounted onto the inner tube of the inhaler article by a user and may be easily removed from the inner tube of the inhaler article by a user.

Mounting and removal of the nicotine powder consumable article may be accomplished by sliding or "skewering" the nicotine powder consumable article onto the inner tube, via for example, laterally sliding or "skewering" the nicotine powder consumable article onto the inner tube along the longitudinal axis toward the air sealing element of the inhaler article. The air sealing element may operate as a physical stop that may register the nicotine powder consumable article with the air flow apertures of the inner tube.

The nicotine powder consumable article may include an elongated consumable body extending between a proximal end and a distal end and a capsule fixed within the elongated consumable body. The capsule may contain particles comprising nicotine or a pharmaceutically acceptable salt thereof. The capsule is disposed onto the inner tube. Preferably, the inner tube extends through opposing sides of the capsule, such that, the tube intake end extends distally from the capsule when the nicotine powder consumable article is received in the consumable receiving end of the holder body.

The nicotine powder consumable article may have any useful diameter to be received within the tubular housing defining the holder body of the inhaler article. The nicotine powder consumable article may tightly fit within tubular housing defining the holder body of the inhaler article. The nicotine powder consumable article may loosely fit within tubular housing defining the holder body of the inhaler article. The nicotine powder consumable article may have an outer diameter being about 80% to about 99% of the inner diameter of the tubular housing defining the holder body of the inhaler article. The nicotine powder consumable article may have an outer diameter being about 85% to about 95% of the inner diameter of the tubular housing defining the holder body of the inhaler article. Any void space defined between the nicotine powder consumable article and the inner diameter of the tubular housing defining the holder body of the inhaler article may not cooperate to form any part of the inhalation air flow channel.

The nicotine powder consumable article may have an elongated cylindrical body extending along a longitudinal axis. Once mounted on the inner tube of the inhaler article, the nicotine powder consumable article may have an elongated cylindrical body extending along the longitudinal axis of the inner tube. Once mounted on the inner tube of the inhaler article, the nicotine powder consumable article may have an elongated cylindrical body that is coaxial with the inner tube or the inner tube and the tubular housing defining the holder body of the inhaler article.

The nicotine powder consumable article may have a substantially uniform outer diameter along the length of the nicotine powder consumable article. The nicotine powder consumable article may have a circular cross-section that may be uniform along the length of the elongated nicotine powder consumable article. The nicotine powder consumable article may have an outer diameter in a range from about 4 mm to about 14 mm, or from about 5 mm to about 10 mm, or about 6 mm to about 10 mm, or about 6 mm to about 8 mm. The nicotine powder consumable article may have a length (along the longitudinal axis) in a range from about 30 mm to about 100 mm, or from about 40 mm to about 80 mm, or about 40 mm to about 60 mm.

The nicotine powder consumable article may be sized to fit or be received within a consumable receiving end of an inhaler device. The nicotine powder consumable article may have a length that exceed a length of a receiving chamber defined by the air sealing element and the consumable receiving end of an inhaler device. The nicotine powder consumable article may have a length that exceed a length of the receiving chamber of an inhaler device such that at least about 10%, or at least about 20% of the length of the nicotine powder consumable article extends distally from the consumable receiving end of an inhaler device. The nicotine powder consumable article may have a length that exceed a length of the receiving chamber of an inhaler device such that at least about 10% to about 50%, or at least about 20% to about 40% of the length of the nicotine powder consumable article extends distally from the consumable receiving end of an inhaler device.

The nicotine powder consumable article may have an outer diameter equal to the diameter of the enclosed capsule, within the nicotine powder consumable article, plus the thickness of the layer or overwrap forming the outer surface of the nicotine powder consumable article. Preferably the layer or overwrap forming the outer surface of the nicotine powder consumable article is tightly wrapped around the capsule and in intimate or direct contact with the capsule. The capsule outer surface and the layer or overwrap forming the outer surface of the nicotine powder consumable article do not provide air flow along the outer surface of the capsule.

The nicotine powder consumable article may have the proximal end and the distal end filled with a material that occludes the movement of the capsule within the nicotine powder consumable article. Preferably this material completely fills the open space defined by the elongated consumable body distal end and proximal end. The material filling the distal end is preferably porous or air permeable to allow inhalation air to easily flow though it to the enclosed capsule. The material filling the proximal end is pierceable by the inner tube. The material filling the proximal end may be a similar porous or air permeable material, or the material filling the proximal end may be a different type of material that may not be as air permeable or porous. The material filling the proximal end may be an air impermeable material.

The material filling the open space defined by the elongated consumable body distal end and proximal end may be plugs of porous material. A first plug of porous material may be disposed within the proximal end of the elongated consumable body and a second plug of porous material may be disposed within the distal end of the elongated consumable body. The first plug of porous material may comprise cellulose acetate tow and the second plug of porous material porous material may comprise cellulose acetate tow. The first plug of porous material and the second plug of porous material may fix the capsule within the elongated consumable body. The first plug of porous material and the second plug of porous material may completely fill the open space defined by the elongated consumable body distal end and proximal ends and contact the capsule, to secure the capsule within the elongated consumable body. The tube intake end of the inner tube preferably extends into the second plug of porous material when the nicotine powder consumable article is mounted onto the inner tube or received within the received in the consumable receiving end of the holder body.

The nicotine powder consumable article may further comprise a flavour delivery element for providing a flavour sensation to a user when the user draws air through the inhaler article. The flavour delivery element is preferably provided in series with the capsule to minimize the impact on the external diameter or width of the nicotine powder consumable article.

As used herein, by "in series" it is meant that the flavour delivery element and the capsule are arranged within the nicotine powder consumable article so that in use an air stream (inhalation air) drawn through the nicotine powder consumable article either passes through the capsule and then passes around the flavour delivery element, or passes around the flavour delivery element and the passes through the capsule.

The flavour delivery element may be provided upstream of the capsule. The flavour delivery element may be provided within the second plug of porous material.

To prevent leakage of a flavourant from the flavour delivery element the flavour delivery element preferably comprises a breakable capsule that may be ruptured by a user squeezing the nicotine powder consumable article about the capsule. Suitable materials for forming a breakable capsule providing a flavour delivery element include, for example, gel forming agents and hydrocolloids such as xanthan gum, gellan gum, carboxymethyl cellulose, carbopol, araboxymethyl cellulose, and combinations thereof. The breakable capsule is preferably breakable under a crushing force of less than about 50 Newtons, optionally less than about 10 Newtons, optionally less than about 5 Newtons. Providing a capsule that breaks at a crushing force within these ranges ensures that it is relatively easy for the user to crush the capsule by hand. Additionally, or alternatively, breaking the breakable capsule may require a crushing force of at least about 3 Newtons, optionally at least about 5 Newtons, optionally at least about 10 Newtons. Providing a capsule that requires a minimum breaking force within these ranges reduces the risk of accidental rupturing of the capsule during manufacture and subsequent handling of the article prior to use.

Alternatively or in addition to a breakable capsule, the flavour delivery element may be a carrier element, such as a thread, impregnated with a flavourant. Preferably, the flavourant in these embodiments is menthol. The thread can be disposed in a plug of porous material that is preferably upstream of the capsule.

In any of the embodiments comprising a flavour delivery element, the flavour delivery element comprises one or more flavourants that may be in the form of a liquid or a solid (at room temperature of about 22 degrees Celsius and one atmosphere pressure). Solid flavourants may be in the form of a powder. Flavourants can include flavour formulations, flavour-containing materials and flavour precursors. The flavourant may include one or more natural flavourants, one or more synthetic flavourants, or a combination of natural and synthetic flavourants. Suitable flavours or flavourants are described above.

The inhaler article and inhaler system may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler article and inhaler system may preferably has a resistance to draw of between about 25 mmWG and about 100 mmWG. Preferably, the inhaler article and inhaler system has a resistance to draw of about 50 mmWG. Resistance to draw is measured in accordance with ISO 6565-2002.

The inhaler may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

The inhaler article and inhaler system will now be further illustrated, by way of example only, with reference to the accompanying drawings.

Figure 1:
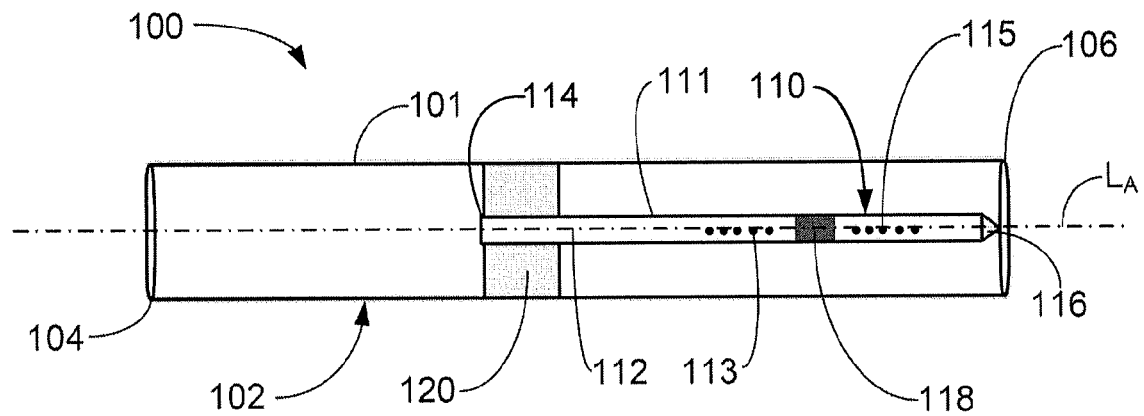
FIG. 1 is a cross-sectional schematic diagram of an illustrative inhaler article.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

FIG. 1 is a cross-sectional schematic diagram of an illustrative inhaler article 100. The inhaler article 100 includes a tubular housing 102 defining a holder body 101 extending along a longitudinal axis LA from a mouthpiece end 104 to a consumable receiving end 106. The holder body 101 includes an inner tube 110 extending along the longitudinal axis LA and within the tubular housing 102 from a tube intake end 116 to a tube exhaust end 114. The tube intake end 116 is proximate the consumable receiving end 106. The inner tube 110 defines an air flow lumen 112 with two or more air flow apertures 113, 115 extending through a wall 111 of the inner tube 110. An air blocking feature 118 is positioned in the air flow lumen 112 and between two of the air flow apertures 113, 115.

The air blocking feature 118 is disposed within the air flow lumen 112 downstream from the tube intake end 116. At least one air flow aperture 115 defines a tube air outlet 115 and is between the blocking feature 118 and the tube intake end 116. At least one air flow aperture 113 defines a tube air inlet 113 and is between the blocking feature 118 and the tube exhaust end 114. The tube exhaust end 114 is in air flow communication with the mouthpiece end 104. The figures illustrate five tube air outlets 115 and five tube air inlets 113, it is understood these apertures 113, 115 may be present in any useful number as described above.

An air sealing element 120 may be positioned within the tubular housing 102 and isolating the mouthpiece end 104 from the consumable receiving end 106. The inner tube 110 extends through the air sealing element 120.

Figure 2:
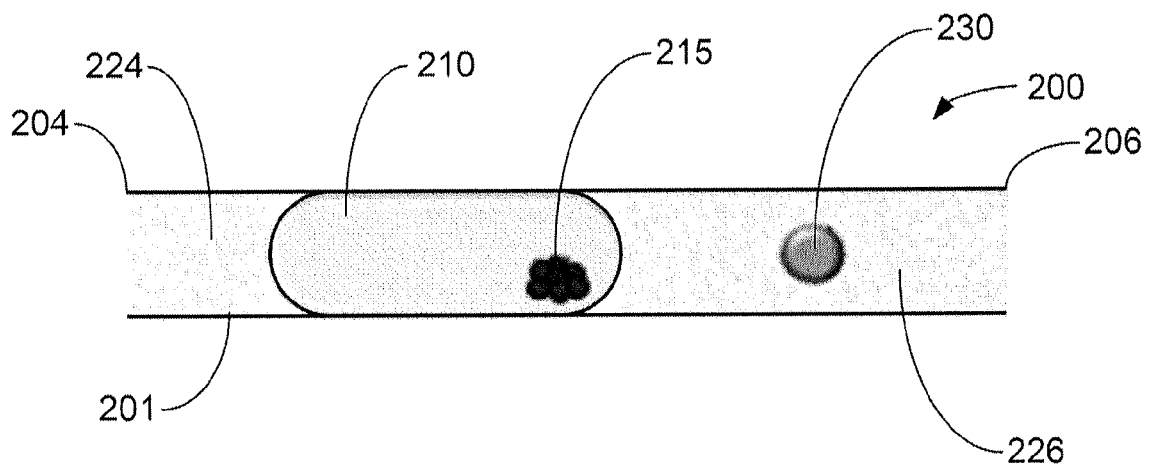
FIG. 2 is a cross-sectional schematic diagram of an illustrative nicotine powder consumable article.

FIG. 2 is a cross-sectional schematic diagram of an illustrative nicotine powder consumable article 200. The nicotine powder consumable article 200 includes an elongated consumable body 201 extending between a proximal end 204 and a distal end 206. A capsule 210 is fixed within the elongated consumable body 201. The capsule 210 contains particles 215 comprising nicotine or a pharmaceutically acceptable salt thereof.

A first plug of porous material 224 may be disposed within the proximal end 204 of the elongated consumable body 201 and a second plug of porous material 226 may be disposed within the distal end 206 of the elongated consumable body 201. A flavour delivery element 230 may be disposed within the second plug of porous material 226.

Figure 3:
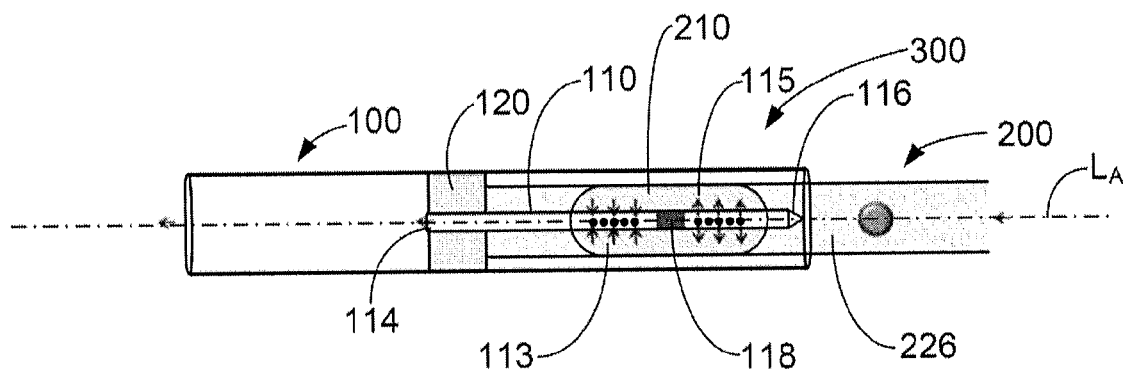
FIG. 3 is a cross-sectional schematic diagram of an illustrative inhaler system including a nicotine powder consumable article received within or onto an illustrative inhaler article.
Figure 4:
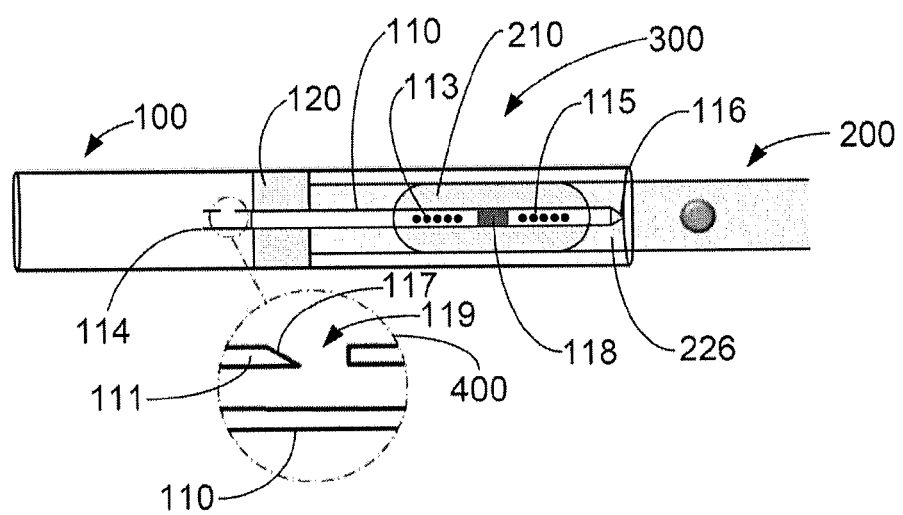
FIG. 4 is a cross-sectional schematic diagram of the inhaler system of FIG. 3 and illustrating a magnified view of an exemplary vibration inducing element.
Figure 5:
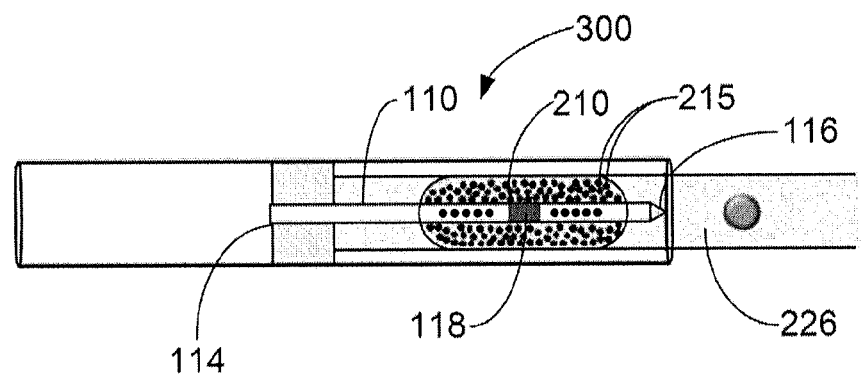
FIG. 5 is a cross-sectional schematic diagram of the inhaler system of FIG. 3 illustrating a fully charged capsule containing particles comprising nicotine.
Figure 6:
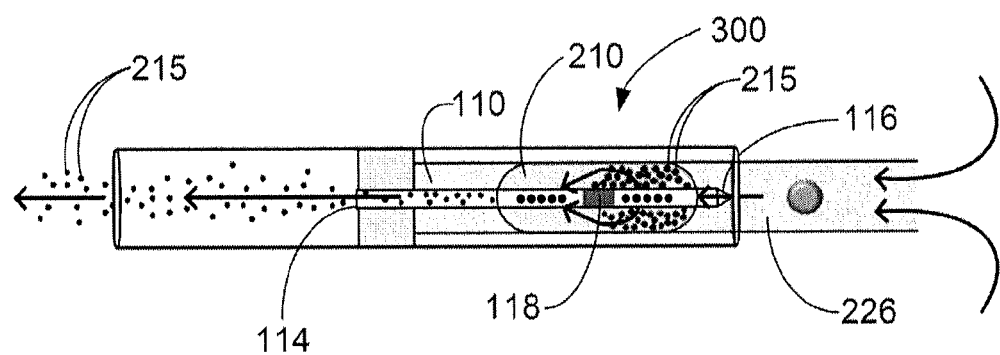
FIG. 6 is cross-sectional schematic diagram of the inhaler system of FIG. 5 illustrating an inhalation airflow though the inhaler article fully charged capsule containing particles comprising nicotine.

FIG. 3 is a cross-sectional schematic diagram of an illustrative inhaler system 300 including a nicotine powder consumable article 200 received within or onto an illustrative inhaler article 100. FIG. 4 is a cross-sectional schematic diagram of the inhaler system 300 of FIG. 3 and illustrating a magnified view 400 of an exemplary vibration inducing element 119. FIG. 5 is a cross-sectional schematic diagram of the inhaler system 300 of FIG. 3 illustrating a fully charged capsule containing particles 215 comprising nicotine. FIG. 6 is cross-sectional schematic diagram of the inhaler system 300 of FIG. 5 illustrating an inhalation airflow (designated with the arrows) though the inhaler article fully charged capsule containing particles comprising nicotine.

The capsule 210 is disposed onto the inner tube 110 and the inner tube extends through opposing sides of the capsule 210. The tube intake end 116 extends distally from the capsule 210 when the nicotine powder consumable article 200 is received in the consumable receiving end 106 of the holder body 101. The tube intake end 116 may extend into the second plug of porous material 226.

The air blocking feature 118 and air flow apertures 113, 115 are positioned within the capsule 210 when the nicotine powder consumable article 200 is received in the consumable receiving end 106 of the holder body 101. The tube intake end 116 may extend distally from the capsule 210 and the tube air outlet 114 may extend proximally from the capsule 210 when the nicotine powder consumable article 200 is received in the consumable receiving end 106 of the holder body 101.

A vibration inducing element 119 may be disposed on the inner tube 110. The vibration inducing element 119 is illustrated disposed on the inner tube 110 proximate to the tube exhaust end 114 in FIG. 4. The vibration inducing element 119 may be configured to operate as a "reed" element, as described above. The vibration inducing element 119 may include an aperture through the wall 111 of the inner tube 110 and having a tapered or angled downstream aperture edge 117.

The invention claimed is:

1. An inhaler article comprising:
    a tubular housing defining a holder body extending along a longitudinal axis from a mouthpiece end to a consumable receiving end, the holder body comprising:
        an inner tube extending along the longitudinal axis and within the tubular housing from a tube intake end to a tube exhaust end, the tube intake end is proximate the consumable receiving end, the inner tube defines an air flow lumen with two or more air flow apertures extending through a wall of the inner tube, an air blocking feature is positioned in the air flow lumen and between two of the air flow apertures;
        a vibration inducing element disposed on the inner tube proximate to the tube exhaust end or the tube intake end, the vibration inducing element comprises an aperture through the wall of the inner tube and having a tapered or angled downstream aperture edge.

2. The inhaler article according to claim 1, wherein the air blocking feature is disposed within the air flow lumen downstream from the tube intake end, at least one air flow aperture defines a tube air outlet and is between the blocking feature and the tube intake end, at least one air flow aperture defines a tube air inlet and is between the blocking feature and the tube exhaust end, the tube exhaust end is in air flow communication with the mouthpiece end.

3. The inhaler article according to claim 2 further comprising an air sealing element positioned within the tubular housing and isolating the mouthpiece end from the consumable receiving end, the inner tube extending through the air sealing element.

4. The inhaler article according to claim 2, wherein the tubular housing and the inner tube are co-axial.

5. The inhaler article according to claim 2, further comprising a capsule disposed onto the inner tube, the inner tube extending through opposing sides of the capsule, the capsule containing particles comprising nicotine or a pharmaceutically acceptable salt thereof.

6. The inhaler article according to claim 1, wherein at least 3 air flow apertures are located upstream from and adjacent to the air blocking feature and at least 3 air flow apertures are located downstream from and adjacent to the air blocking feature.

7. The inhaler article according to claim 1, further comprising an air sealing element positioned within the tubular housing and isolating the mouthpiece end from the consumable receiving end, the inner tube extending through the air sealing element.

8. The inhaler article according to claim 1, wherein the tubular housing and the inner tube are co-axial.

9. The inhaler article according to claim 1, further comprising a capsule disposed onto the inner tube, the inner tube extending through opposing sides of the capsule, the capsule containing particles comprising nicotine or a pharmaceutically acceptable salt thereof.

10. The inhaler article according to claim 9, wherein the air blocking feature and air flow apertures are positioned within the capsule and the tube intake end extends distally from the capsule and the tube air outlet extends proximally from the capsule.

11. An inhaler system comprising:
    an inhaler article according to claim 1;
    a nicotine powder consumable article configured to be received in the consumable receiving end of the holder body, the nicotine powder consumable article comprising:
        an elongated consumable body extending between a proximal end and a distal end; and
        a capsule fixed within the elongated consumable body, the capsule containing particles comprising nicotine or a pharmaceutically acceptable salt thereof;
    the capsule disposed onto the inner tube and the inner tube extending through opposing sides of the capsule, the tube intake end extends distally from the capsule when the nicotine powder consumable article is received in the consumable receiving end of the holder body.

12. The inhaler system according to claim 11, wherein a first plug of porous material is disposed within the proximal end of the elongated consumable body and a second plug of porous material is disposed within the distal end of the elongated consumable body.

13. The inhaler system according to claim 12, wherein the first plug of porous material comprises cellulose acetate tow and the second plug of porous material porous material comprises cellulose acetate tow.

14. The inhaler system according to claim 13, wherein the first plug of porous material and the second plug of porous material fix the capsule within the elongated consumable body.

15. The inhaler system according to claim 14, wherein the second plug of porous material contains a flavour delivery element.

16. The inhaler system according to claim 15, wherein the tube intake end extends into the second plug of porous material.

17. The inhaler system according to claim 13, wherein the tube intake end extends into the second plug of porous material.

18. The inhaler system according to claim 12, wherein the first plug of porous material and the second plug of porous material fix the capsule within the elongated consumable body.

19. The inhaler system according to claim 12, wherein the second plug of porous material contains a flavour delivery element.

20. The inhaler system according to claim 12, wherein the tube intake end extends into the second plug of porous material.

* * * * *